United States Patent [19]
Darby et al.

[11] Patent Number: 5,275,620
[45] Date of Patent: Jan. 4, 1994

[54] IMPLANTABLE LEAD CONNECTORS AND REMOTE LEAD ASSEMBLY

[75] Inventors: Peter Darby, Eastwood; Akira Nakazawa, Balmain, both of Australia

[73] Assignee: Telectronics, N.V., Curacao, Netherlands

[21] Appl. No.: 526,031

[22] Filed: May 21, 1990 (Under 37 CFR 1.47)

[51] Int. Cl.$^5$ .............................................. A61N 1/00
[52] U.S. Cl. ................................. 607/1; 439/775
[58] Field of Search .............. 128/419; 439/775, 817

[56] References Cited

U.S. PATENT DOCUMENTS

| | | | |
|---|---|---|---|
| 781,091 | 1/1905 | Phillips | 439/817 |
| 2,685,679 | 8/1954 | Sam | 339/258 |
| 3,375,749 | 4/1968 | Coldren et al. | 85/80 |
| 3,508,538 | 4/1970 | Keller, Jr. | 128/697 |
| 3,596,229 | 7/1971 | Hoborst | 339/61 R |
| 3,806,860 | 4/1974 | Flammini | 439/817 |
| 4,112,953 | 9/1978 | Shanker et al. | |
| 4,141,752 | 2/1979 | Shipko . | |
| 4,142,532 | 3/1979 | Ware . | |
| 4,202,592 | 5/1980 | Rullier et al. . | |
| 4,245,642 | 1/1981 | Skubitz et al. . | |
| 4,262,673 | 4/1981 | Kinney et al. . | |
| 4,278,093 | 7/1981 | Lafortune et al. . | |
| 4,316,471 | 2/1982 | Shipko et al. . | |
| 4,347,849 | 9/1982 | Congdon | 128/419 P |
| 4,942,876 | 7/1990 | Gotthardt | 128/419 P |

FOREIGN PATENT DOCUMENTS

| | | |
|---|---|---|
| 310985 | 9/1917 | Fed. Rep. of Germany ... 21C/21 C |
| 1213508 | 3/1966 | Fed. Rep. of Germany ......................... 21C/21/01 |
| 1270149 | 6/1968 | Fed. Rep. of Germany ......................... 21C/21/01 |
| 2345832 | 10/1977 | France . |
| 2383532 | 10/1978 | France . |
| 89/05170 | 6/1989 | PCT Int'l Appl. ........... A61N 1/375 |

*Primary Examiner*—William E. Kamm
*Assistant Examiner*—Kennedy J. Schaetzle
*Attorney, Agent, or Firm*—Gottlieb, Rackman & Reisman

[57] ABSTRACT

This invention describes novel lead connectors for use with an implantable device, such as a cardiac pacemaker. In one aspect, the connectors use resilient spring action to mechanically retain the lad in the connector and maintain reliable electrical contact. In another aspect, the connector has a plurality of terminations which are grouped together and is enclosed in a biocompatible flexible insulator to form a connector strip. A remote lead assembly is also provided, which permits the implanted device to be remotely located from the connectors used to connect with leads coupled to implanted electrodes.

5 Claims, 6 Drawing Sheets

IMPLANTABLE LEAD CONNECTORS AND REMOTE LEAD ASSEMBLY

BACKGROUND OF THE INVENTION

The present invention relates to an implantable connector and remote connector assembly for coupling electric leads to implantable devices.

Body implantable electronic devices capable of artificially stimulating an organ, such as the heart, to correct or modify its behavior are well known. In the case of the heart, stimulation is accomplished by transmitting electrical impulses from an implanted cardiac device via electrical leads to electrodes disposed in appropriate areas of the heart muscle tissue. Several different types of impulse-generating devices have been developed to provide a variety of electrical impulses in response to various organ malfunctions.

Generally speaking, most devices which are implantable comprise (1) a small, self-contained sealed unit which includes a source of electrical energy, and (2) an electronic device for producing impulses at appropriate intervals. After preliminary testing of the device, it is surgically implanted into a subcutaneous cavity. Electrodes at one end of electrical leads are implanted in the organ tissue, while the other end of the electrical leads extend to the device and are coupled to it so a to provide the necessary electrical connection.

Figures 1A, 1B, 2:
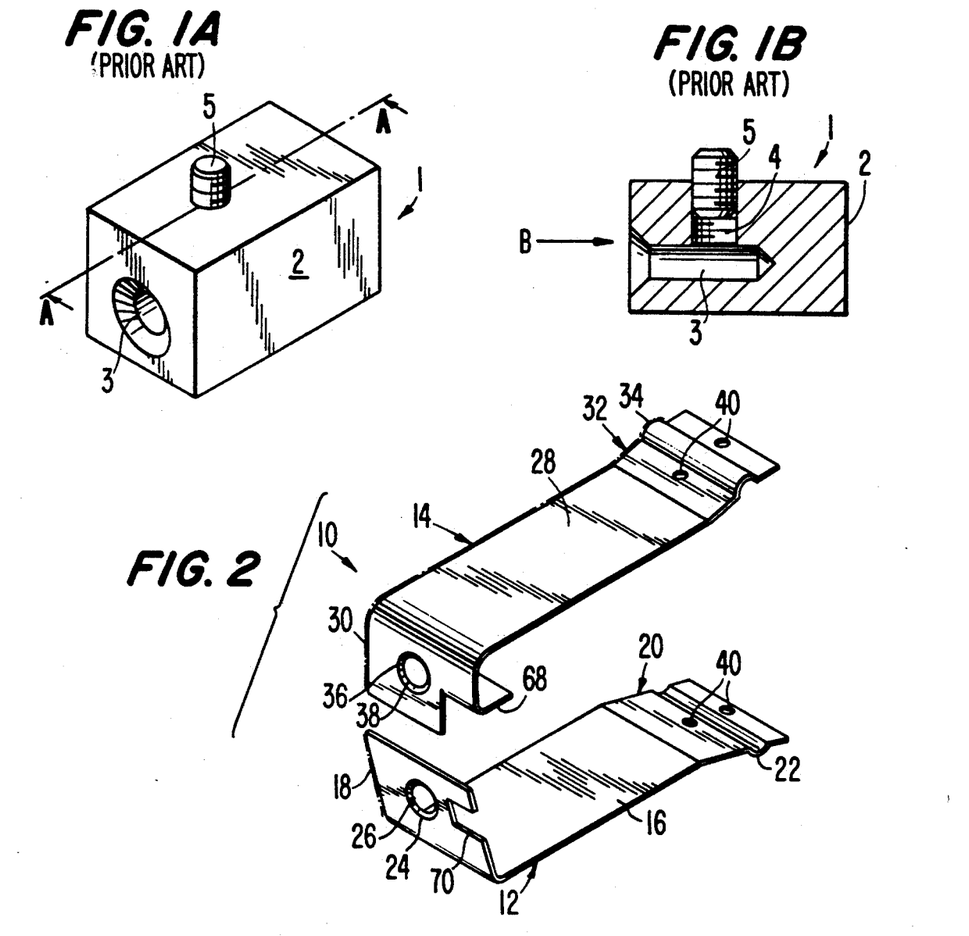
FIG. 1A is a perspective view of a prior art connector having a set screw arrangement.
FIG. 1B is a cross-sectional view of the prior art connector of FIG. 1A along lines A—A.
FIG. 2 is an exploded perspective view showing the two halves of a connector assembly according to a first embodiment of the present invention.

Conventional methods of coupling electrical leads to the device are comparatively elaborate. An example of such a convention coupling device is shown in FIGS. 1A and 1B. To couple or terminate a lead, the device 1 is provided with a female conductive member 2 having an elongated passage 3 for receiving a male electrode tip member (not shown) attached to the end of the electrical lead. A threaded hole 4 extends through the side of female member 2 into passage 3. The male member is slipped into the passage (in the direction of arrow B in FIG. 1B) and a set screw 5 is then screwed into threaded hole 4 by means, such as a small wrench (not shown), which tightly urges screw 5 against the side of the male connector. This procedure is repeated for every electrical lead being coupled to the implanted device.

Because devices such as cardiac pacemakers must remain in the body for years, electrical leads need to be reliable. Several problems could occur if the leads are not connected in such a way that body fluids are inhibited from contact with the conductive portions of the leads. For instance, electrolysis could occur at the connection with the male member of the lead, causing the connection to deteriorate. A conductive path of body fluids could also cause attenuation of electric signals passing through the connection and, in the case of multiple connections, cause electrical crosstalk. Furthermore, the seals which are described in the prior art necessitate the manipulation of extremely small screws, seals and the like, which is both time consuming and difficult.

Previously the leads for implanted devices have been terminated in a connector that is rigidly attached to the device. This requires the leads to be taken from the site they stimulate, known as the lead to body interface, to the site of the implanted device. A device which is implanted a remote distance from a plurality of lead to body interfaces requires a surgeon performing the implant to route the leads a relatively long distance through the body between the device and site to be stimulated, referred to as "tunnelling." When either the implanted device or the implanted lead must be removed or serviced, it is frequently necessary to also remove the electrode lead and subsequently perform another tunnelling operation. This adds to the length and complexity of the surgical procedure, both of which are undesirable results.

SUMMARY OF THE INVENTION

The present invention provides a new and improved means of terminating a plurality of implantable electrode leads.

In particular, the present invention avoids the use of set screws and seals in the connector, eliminates and simplifies operations otherwise needed to connect the lead, and reduces the probability of body fluid contact with the electrical connection through the set screw access.

The invention also provides a means for routing one or more signal lines from the impulse-generating device in a single insulated cable to a site where it is more convenient for the surgeon to terminate the leads to a connector, thereby avoiding multiple tunnelling operations.

Other advantages provided by the present invention will become apparent from the following disclosure.

According to the present invention, an implantable conductive connector for coupling with a conductive electrode tip at a distal end of a pacemaker lead, the connector comprising: first means for receiving the electrode tip; and second means for resiliently engaging the first means for entrapping the electrode tip between the first means and the second means to provide electrical and mechanical coupling with the electrode tip, the first and second means being resiliently disposed in a closed position prior to insertion of the electrode tip into the connector, and being disposed in an open position, different from the closed position, upon insertion of the electrode tip into the connector.

The present invention further provides a connector wherein the terminal ends of more than one electrode leads can be linked together by an insulated biocompatible flexible polymer strip, with the strip then being linked to an implantable device by a single cable comprising more than one insulated conductors.

The accompanying drawings, which are incorporated in and constitute a part of this specification, illustrate embodiments of the present invention and, together with the description, serve to explain the principles of the invention.

DESCRIPTION OF THE PREFERRED EMBODIMENTS

According to the present invention, an implantable conductive connector is provided for coupling with a conductive electrode tip at a distal end of a pacemaker lead, the connector comprising first means for receiving the electrode tip and second means resiliently engaging the first means for entrapping the electrode tip between said first means and the second means to provide electrical and mechanical coupling with the electrode tip. The first and second means are resiliently disposed in a closed position prior to insertion of the electrode tip into the connector, and are disposed in an open position, different from the closed position, upon insertion of the electrode tip into the connector.

Figure 3:
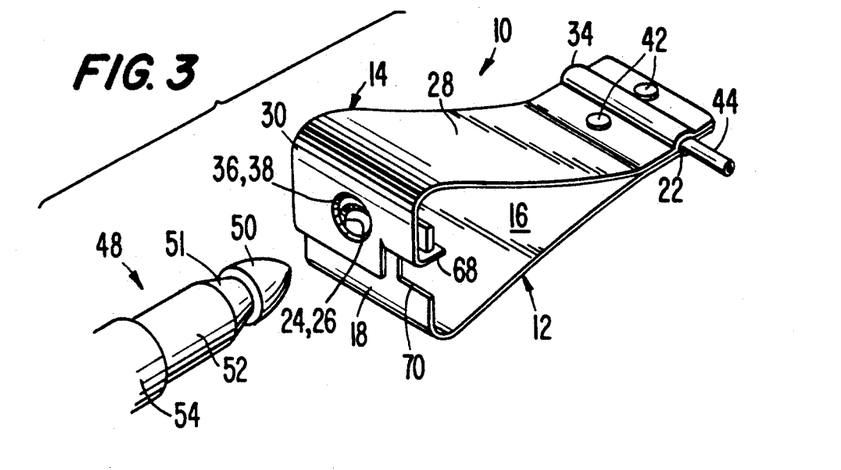
FIG. 3 is a perspective view of the connector assembly of FIG. 2 depicting insertion of an electrode tip into the connector.
Figure 5:
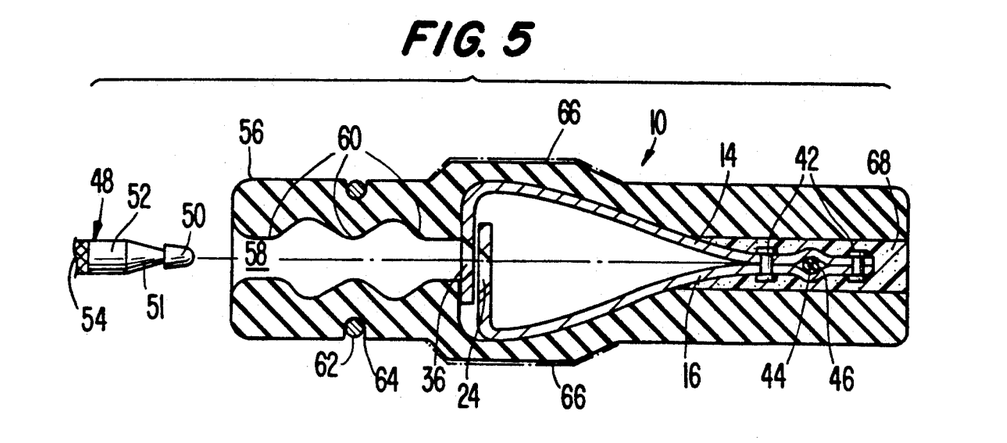
FIG. 5 is a cross-sectional view of the connector assembly of FIGS. 4A–4C, taken along line A—A of FIG. 4A; including a diagrammatic depiction of the tip of an electrode lead.

FIGS. 2, 3 and 5 illustrate a first preferred embodiment of the connector according to the present invention, in which the connector is generally represented by reference character 10. In the embodiment illustrated, the first means are denoted by reference character 12 and the second means are denoted by reference character 14. Throughout the drawings, like numbers will be used for like elements for sake of clarity.

First means 12 comprises a cantilevered flexible strip having a generally planar portion 16, shaped at one end with an angled face 18 and, at the other end 20, with an indented channel portion 22. Face 18 is provided with a first hole 24, which preferably has an internal chamfered edge 26.

Second means 14 likewise comprises a cantilevered flexible strip having a generally planar portion 28, shaped at one end with an angled face 30 and, at the other end 32, with an indented channel portion 34. Face 30 is provided with a second hole 36, which preferably has an internal chamfered edge 38.

The cantilevered strips 12 and 14 are preferably formed of a conductive material, such as stainless steel or titanium. Alternately, the strips may be molded of a plastic material with conductive inserts suitable for conducting signals in the manner described below or the plastic can be rendered electrically conductive.

The strips 12 and 14 are joined together proximate ends 20 and 32, as shown best in FIGS. 3 and 5. To facilitate this connection, each strip 12, 14 may be provided with a set of holes 40 (FIG. 2) into which rivets 42 are positioned for purposes of joining together the strips (FIGS. 3 and 5). Other means suitable for joining the strips together may be employed, such as spot welding and the like, without departing from the spirit or scope of the invention.

Channel portions 22 and 34 serve to encapture and couple, both mechanically and electrically, conductor 44. This conductor may be provided with an insulating sheath 46 (FIG. 5), provided the insulation has been suitably removed to facilitate electrical contact with a portion of strips 12 and 14. Conductor 44 may form one conductor of an electrode lead (not shown) that is connected to either the implanted pacemaker device or to the implanted electrode terminal used for pacing and/or sensing purposes.

FIGS. 3 and 5 illustrate the manner in which an electrode tip 48 may be inserted and held in place by connector 10. Tip 48 has a tapered head 50 mounted on a shaft 52 via a beveled shoulder portion 51, all of which are formed of a conductive material such as titanium or stainless steel. An insulating sheath 54 may also be provided, in known fashion.

In the "closed" position of connector 10—namely, the position of the connector prior to or in the absence of insertion of electrode tip 48—strips 12 and 14 are resiliently coupled together so that respective holes 24 and 36 are slightly misaligned. Compression of strips 12 and 14 relative each other causes alignment of holes 24 and 36 so that the tapered head 50 and shaft 52 of electrode tip 48 may be inserted. This compression may be accomplished by manually pressing together strips 12 and 14 along their respective planar portions 16, 28.

Because the two strips are cantilevered, head 50 of electrode tip 48 cannot be inserted farther than the point at which the two strips are joined, e.g., up to the position of the left most rivet 42 in FIGS. 3 and 5. Once manual compression of strips 12 and 14 has stopped, the resilience of the two strips causes them to try to move apart, whereupon electrode tip 48 is captured in holes 36, 38 due to the interference of chamfered edges 26, 38. In this fashion, both mechanical and electrical connection with electrode tip 48 is achieved by connector 10.

Figure 4A:
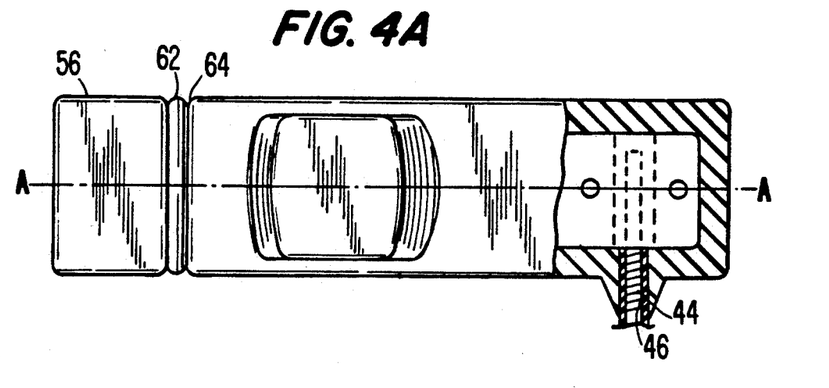
FIG. 4A is a side plan view of the connector assembly of FIG. 2, as surrounded by a flexible biocompatible insulative material.
Figure 4B:
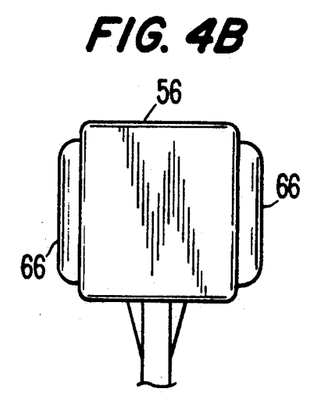
FIG. 4B is an end plan view of the connector assembly of FIG. 4A.
Figure 4C:
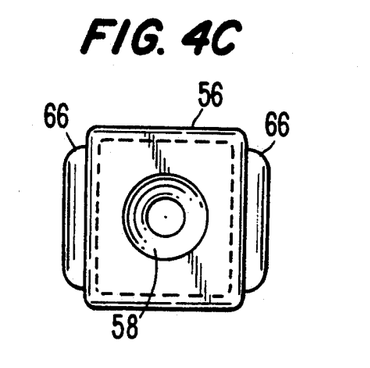
FIG. 4C is an opposite end plan view of the connector assembly of FIG. 4A.

FIGS. 4 and 5 illustrate details of a housing 56 that may be placed about connector 10 to prevent ingress of fluids and degradation of the connector. The housing 56 is denoted by reference character 56. It is preferably formed of a biocompatible insulating material, such as silicon rubber or the like.

Housing 56 has a passageway 58 extending from one end that is aligned to permit entry and removal of electrode tip 48 relative connector 10. Disposed internally within housing 56 proximate passageway 58 are a plurality of sealing ridges 60 which seal body fluids out of the connector once the electrode tip is inserted. This is accomplished by the diameter of tip shaft 52 being greater than that of the opening through the sealing ridges, thus causing the ridges to compress onto the lead exterior after insertion. Additional sealing is obtained by a suture 62 located in groove 64 above one of the sealing rings 60. This suture can be tightened after the lead insertion, further compressing the sealing ridge onto the lead.

To aid in locating where manual pressure is to be applied to compress connector 10, a pair of raised pads 66 may be provided on the outside of housing 56 adjacent the planar portions of strips 12 and 14. The end of housing 56 proximate conductor 44 and insulation 46 may be sealed, such as with a silicon glue 68 or the like, to prevent ingress of fluids into the region of the connector 10.

Although the strips 12, 14 have been described as being formed of separate pieces of metal or plastic, it is envisioned that these elements may be formed as a unitary piece provided sufficient resilience is presented to accomplish the mechanical and electrical coupling described above. Furthermore, as shown in FIGS. 2 and 3, strips 12 and 14 may be provided with an interlocking tab arrangement comprising a tab 68 and groove 70. This feature serves to prevent the strips 12, 14 from coming too far apart when in the closed position by limiting the degree of travel the strips may move relative each other. While FIGS. 2 and 3 depict the tab as being on strip 14 and the groove as being on strip 12, these relationships may be reversed. Additionally, other arrangements for limiting relative travel of the two strips may be employed without departing from the spirit or scope of the invention.

Figure 6:
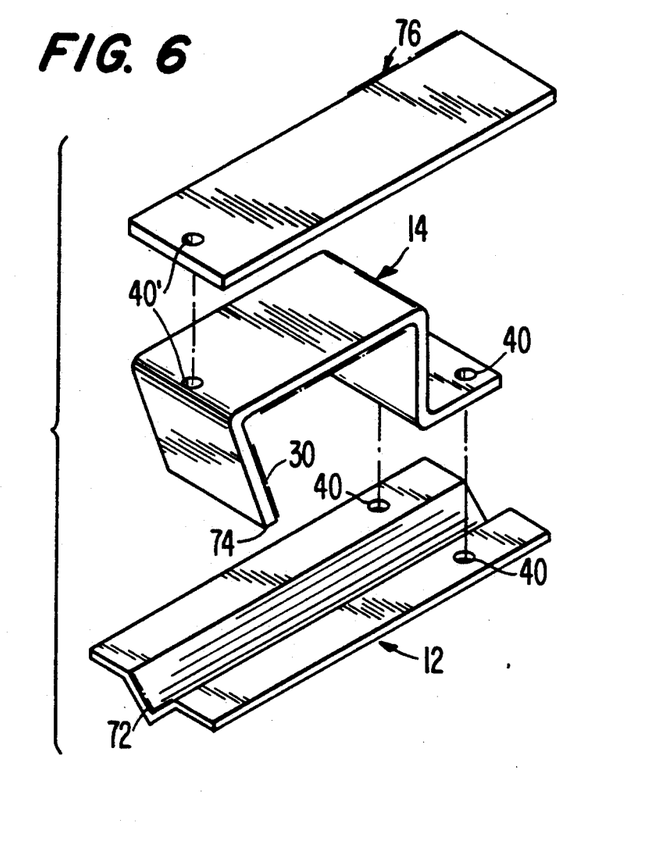
FIG. 6 is an exploded perspective view showing components of a connector assembly according to a second embodiment of the present invention.
Figure 7:
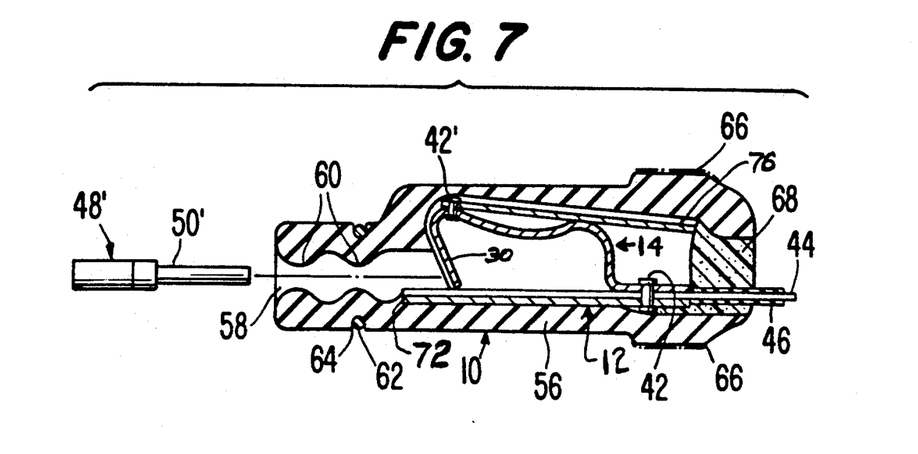
FIG. 7 is a cross-sectional view of the connector assembly of FIG. 6, showing encapsulation of the assembly in a biocompatible insulative housing and including a diagrammatic depiction of the tip of an electrode lead.

FIGS. 6 and 7 illustrate a second embodiment of a connector according to the present invention. The same reference characters have been used to denote like elements shown in FIGS. 2-5. In this second embodiment, second means 14 acts as a cantilever spring arm relative to first means 12. First means 12 is substantially planar, although it is provided with a groove 72 that can receive the conductive portion of an electrode tip 48'. As shown in FIG. 7, electrode tip 48' in this embodiment comprises a straight electrode 50'; however, the tapered arrangement depicted in FIG. 5 may also be employed with this embodiment.

Second means 14, cantilevered relative to first means 12, has a face portion 30 which terminates in an angled edge 74. Mounting atop second means 14 is a lever arm 76 which is used to exert manual pressure so as to open second means 14 relative to first means 12. To couple lever arm 76 to the cantilever strip 14, suitable rivet holes 40' may be provided with a rivet 42' placed therein. Other mounting arrangements may be used, however, such as spot welding; alternately, elements 14 and 76—and even element 12—may be formed of a single piece. These elements may be constructed of conductive materials, such as stainless steel or titanium, or may be molded of plastic with suitable conductive inserts or otherwise rendered electrically conductive.

In the embodiment of FIGS. 6-7, the entry of lead 48' forces cantilever spring arm 14 open, driving edge 74 into the lead tip 50'. Opening of strip 14 is also facilitated by manually pressing upon lever arm 76, i.e., in the region of pads 66 on the outside of biocompatible housing 58. Any attempt to withdraw the lead tip without releasing the cantilever spring causes the over-center face section 30 of the cantilever to attempt to return to center, against the resilience of the end of strip 14, and driving the edge into the tip, increasing further the difficulty of removing the lead from the connector.

Figures 8, 9:
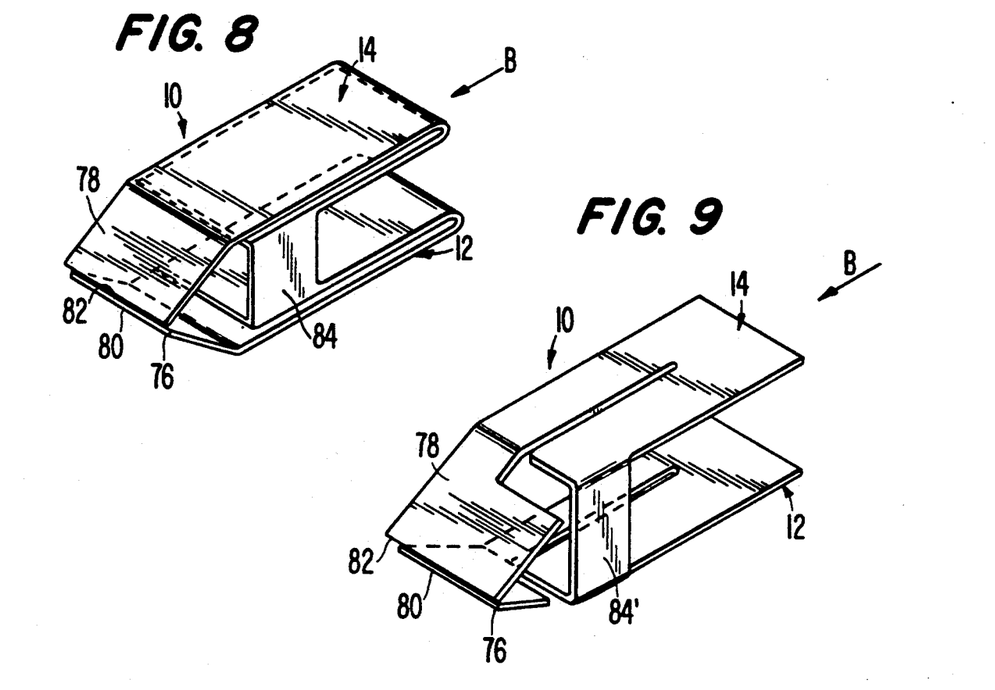
FIG. 8 is a perspective view of a connector assembly according to a third embodiment of the present invention.
FIG. 9 is a perspective view of a connector assembly according to a fourth embodiment of the present invention.

Many other variations of connector 10 are possible in accordance with the present invention. For example, FIGS. 8 and 9 show two alternative unipolar metal spring clips that comprise connector 10. The direction of the lead insertion is shown by the arrows labelled "B". In these embodiments, each of first strip 12 has an angled face portion 76 and each of second strip 14 has an angled face portion 78. Face portions 76 and 78 are angled towards each other, as shown in FIGS. 7 and 8.

Each face portion 76, 78 is provided with a respective edge 80, 82 which serves to capture the electrode tip (not shown) upon insertion into the connector. The electrode tip may be provided with a tapered head, as shown in FIGS. 3 and 5, or may be straight, as shown in FIG. 7; other shapes for the electrode tip may also be employed without departing from the spirit or scope of the invention.

In the embodiments illustrated in FIGS. 8 and 9, strips 12 and 14 are joined by an intermediate region. In FIG. 8, this region is identified by reference character 84, whereas in FIG. 9, this region is identified by reference character 84'. The strips and intermediate region may be formed of a unitary metallic strip, such as titanium or stainless steel, as shown in the Figures. Alternately, separate elements may be used to form each of strips 12, 14 and region 84, 84' provided these elements are joined together in a manner that yields flexible movement of strip 12 relative to strip 14.

The retaining action of the connectors shown in FIGS. 8 and 9 is similar to that described in FIG. 6, wherein the clamping action of edges 80 and 82 serve to mechanically and electrical couple the electrode tip (not shown) with the connector. Release of the electrode tip is achieved by pinching the ends of the connector along strips 12, 14 opposite the ends where face portions 76 and 78 are provided. To seal against ingress of fluids following implantation, the connectors of FIGS. 8 and 9 may be housed within a biocompatible material in the manner described above with respect to FIGS. 4-5 and 7.

The connector assembly according to the present invention may also be used to provide coupling to a multiconductor electrode tip. This arrangement is useful in situations in which more than one conductor is required to carry signals between the implanted cardiac device and the electrodes placed in the patient. For example, the implanted device may be attached to electrodes placed at different locations within the patient or it may be perform a variety of functions and, thus, need more than one electrode for such various sensing and-/or pacing functions.

Figure 10A:
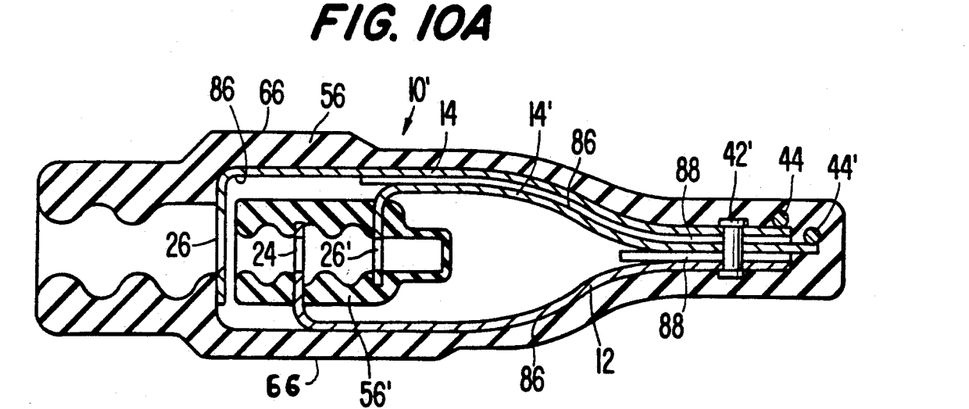
FIG. 10A is a cross-sectional view of a multiple conductor connector assembly according to the present invention.
Figure 10B:
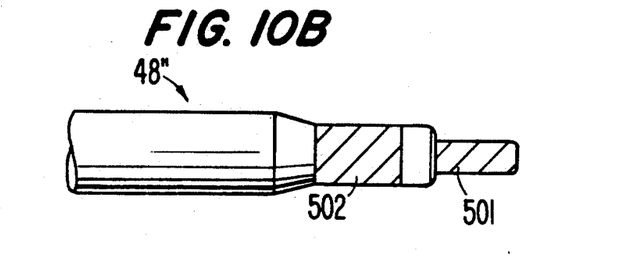
FIG. 10B is a side plan view of an electrode tip for use with the connector assembly of FIG. 10A.

FIG. 10A shows a bipolar connector assembly enabling connection with a corresponding bipolar electrode tip, which is illustrated in FIG. 10B. Bipolar electrode tip, generally designated by reference character 48''', has two separate conductive regions, designated by reference characters 501 and 502. These regions 501, 502 are coupled by known means to respective electrodes or the like (not shown).

The bipolar connector 10' of FIG. 10A is of a construction and design similar to that depicted in FIGS. 2-3 and 5, as described above. Since the same reference characters have been used to designate like elements throughout the Figures, the following description focuses on those elements which differ from the previously described embodiments. Bipolar connector 10' comprises three strip sections, labelled 12, 14 and 14'. Each section has an angled face that includes a hole 24, 26 and 26', respectively, that is of a diameter sufficient to permit entry of conductive regions 501 and 502.

According to a preferred embodiment, each section 12, 14 and 14' is made of metal, such as titanium or stainless steel, coated with an insulating material 86, such as Teflon or the like. Additional insulator strips 88 may also be provided between sections 12, 14 and 14'. The entire assembly is held together by an insulated rivet 42'. Conductors 44 and 44' are spot welded to strips 14 and 14', respectively, which are the strips that ultimately make contact with electrode tips 502 and 501, respectively. Reference character 56' denotes a rubber boot within housing 56 that specifically serves to insulate any electrical signals which may otherwise travel between electrode tip 501 and the ring electrode 502 when lead 48'' is inserted into connector 10'.

Operation of connector 10' is similar to that described above with respect to the embodiment shown in FIG. 5. Specifically, strips 14 and 14' are compressed towards strip 12 so as to align holes 24, 26 and 26' whereafter electrode lead 48'' may be inserted. The dimensions of the electrode lead, conductive regions, holes and boot 56' prevent the lead from being inserted too deeply into connector assembly 10'. Upon release of the compressive force, which may be manually applied conveniently via raised pads 66 on housing 56, strips 12, 14 and 14' attempt to move apart which causes electrode lead 48'' to be firmly held in place. To aid in this function, one or more of holes 24, 26 and 26' may be provided with chamfered edges, as described previously with respect to the embodiment shown in FIGS. 2-3 and 5.

In the connector assembly shown in FIGS. 10A and 10B, tip electrode 501 is arranged to be electrically coupled to strip 14' whereas ring electrode 502 is arranged to be electrically coupled to strip 14. Strip 12 essentially serves the purpose of providing mechanical interaction relative to strips 14 and 14' sufficient to hold electrode lead 48'' in place. It is within the scope of the present invention to add other strips 12, 14 and 14' in order to accommodate leads having more conductors than the bipolar arrangement shown in FIGS. 10A and 10B.

Figure 11:
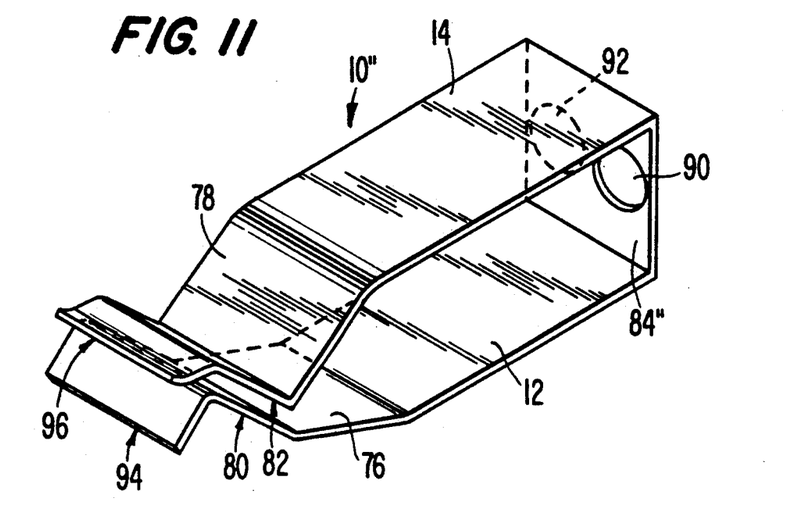
FIG. 11 is a perspective view of a connector assembly according to a fifth embodiment of the present invention.

Another embodiment of a connector according to the present invention is illustrated in FIG. 11, wherein the connector is generally designated by reference character 10''. Connector 10'' is similar in design to the connectors illustrated in FIGS. 8-9 and discussed above. Accordingly, the following discussion focuses on those features of connector 10'' which differ from the previously discussed embodiments.

Connector 10'' includes a pair of strip elements 12 and 14, each of which has an angled face 76 and 78, respectively, and edges 80 and 82, respectively. Strip elements 12 and 14 are joined by an intermediate portion 84'' and, for convenience, all three elements may be formed from a unitary piece of metal, such as titanium or stainless steel, that has a degree of resilience sufficient to all secure capture of an electrode lead tip (not shown) between edges 80 and 82. Portion 84'' is provided with a first hole 90 into which the electrode lead tip (not shown) is inserted. Thus, first hole 90 is aligned with the edges 80, 82 of angled faces 76, 78.

Portion 84'' is also provided with a second hole 92 which is displaced relative to edges 80, 82 as shown in FIG. 11. Instead, hole 92 is aligned with a portion of angled faces 78, 80 that is provided with a flared or rounded extension 94, 96. The purpose of hole 92 and flairs 94, 96 is to allow insertion of a nonconductive pin used to open and close connector 10'' so that an electrode lead may be more easily inserted and removed. This feature is best understood by also referring to FIGS. 12 and 13.

Figure 12:
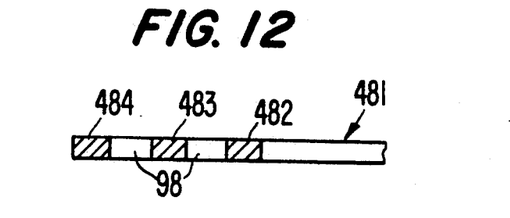
FIG. 12 is a side plan view of an electrode tip for use with the connector assembly of FIG. 11.

The present invention contemplates use of a plurality of connectors 10'' in order to couple to a corresponding plurality of electrode regions of a multiconductor electrode lead. Such an electrode lead is shown in FIG. 12 and is generally designated by reference character 481. Lead 481 has a plurality of individual conductive electrode regions, designated by reference characters 482, 483 and 484. Each region is separated by a respective insulating portion 98. Although FIG. 12 illustrates three conductive regions, it is understood that fewer or additional regions may be employed within the spirit and scope of the present invention.

Figure 13A:
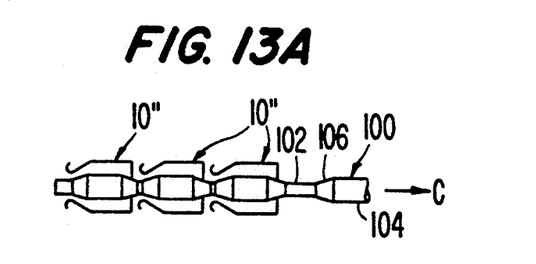
FIG. 13A is a diagrammatic depiction of the connector assembly of FIG. 11, showing the assembly in a closed position.
Figure 13B:
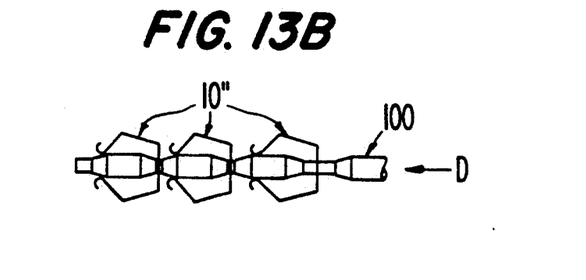
FIG. 13B is a diagrammatic depiction of the connector assembly of FIG. 11, showing the assembly in an open position.

To provide coupling with electrode tip 481, a corresponding plurality of connectors 10'' may be placed in series, i.e., ganged together, in the manner shown diagrammatically in FIGS. 13A and 13B. In such an arrangement, the connectors 10'' are aligned behind each other so that holes 90 and 92 of the connectors are axially aligned. Various methods may be used to achieve such alignment, such as by molding all of the ganged connectors within a common housing formed of a biocompatible insulating material. Other mechanical arrangements may also be employed, provided suitable insulation is provided between the various connectors 10'' so as to avoid electrical interference from occurring.

To open or close connectors 10'' as ganged together in FIGS. 13A and 13B, a nonconductive pin 100 is inserted into aligned holes 92 of the connectors. Pin 100 has a plurality of working regions, each comprising a narrow neck 102, a broad neck 104 and a bevelled shoulder 106 connecting necks 102 and 104. All of these regions are of a diameter sufficient to pass through holes 92, with the diameter of broad neck portion 104 being substantially the same as the diameter of conductive regions 482-484.

To open ganged connectors 10'' so that multiconductor electrode tip 481 can be received, nonconductive pin 100 is inserted through the aligned holes 92 in the direction D shown in FIG. 13B. This insertion is to a depth sufficient to interpose the broad neck portion 104 of pin 100 between each set of flairs 94, 96 of connectors 10''. This opens edges 80 and 82 of each of connectors 10'' so that the multiconductor electrode tip 481 can easily be inserted into the ganged connectors. To accomplish this result, it is necessary that the broad neck portions 104 of pin 100 be arranged so as to correspond to the spacing between the plurality of connectors 10''.

After lead 481 has been inserted into the ganged connectors, pin 100 can be removed, as indicated by arrow C in FIG. 13A. This permits edges 80, 82 of each connector 10" to encapture the corresponding one of conductive regions 482-484 of electrode lead 481 in the manner described previously.

Removal of electrode lead 481 from the ganged connectors is accomplished in a similar manner, i.e., by inserting pin 100 so as to open each connector 10". Thus, the embodiment illustrated in FIGS. 11-13 allows for convenient insertion and removal of an electrode lead from a plurality of ganged connectors.

According to another aspect of the present invention, a remote lead assembly is provided in which the implanted cardiac device is coupled to a lead assembly which, in turn, is coupled to the electrode leads implanted in the various places within the patient. Such an arrangement in diagrammatically depicted in FIGS. 14A and 14B, in which the cardiac device is generally designated by reference character 200 and the remote lead assembly is generally designated by reference character 202.

Figure 14A:
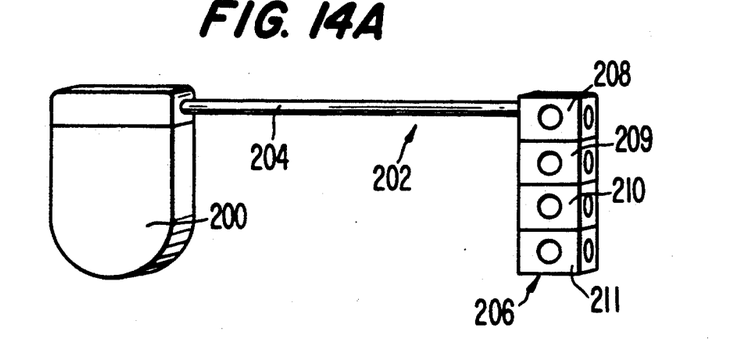
FIG. 14A is a diagrammatic depiction of an implantable cardiac device and remote connector assembly according to the present invention, in which the assembly is connected to the device.
Figure 14B:
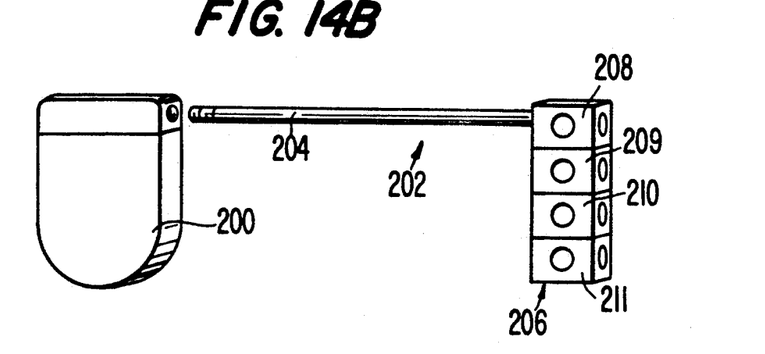
FIG. 14B is a diagrammatic depiction of the remote connector assembly of FIG. 14A, in which the assembly is disconnected from the device.

According to this aspect of the invention, remote lead assembly 202 includes a length of multiconductor cable 204 which has at one end a plurality of connectors 206 to which a corresponding plurality of electrode leads (not shown) may be individually coupled. The opposite end of lead 204 is adapted to be connected to the pacemaker device 200, as shown in FIG. 14A, and may be removable from the device, as shown in FIG. 14B. Such attachment may be accomplished through a wide variety of known terminal arrangements and need not be described herein for purposes of understanding the present invention.

The arrangement shown in FIGS. 14A and 14B permits device 200 to be placed a distance from the plurality of connectors 206 to which the electrode leads can be attached (not shown). Thus, if servicing of either the device or the electrode leads is required, such can be performed simply by disconnecting the appropriate end of remote lead assembly 202. The lead assembly 202 can remain in place, thereby avoiding the necessity of subsequent surgical "tunnelling" procedures that otherwise would be needed to reroute the electrode leads after such servicing.

Figure 15:
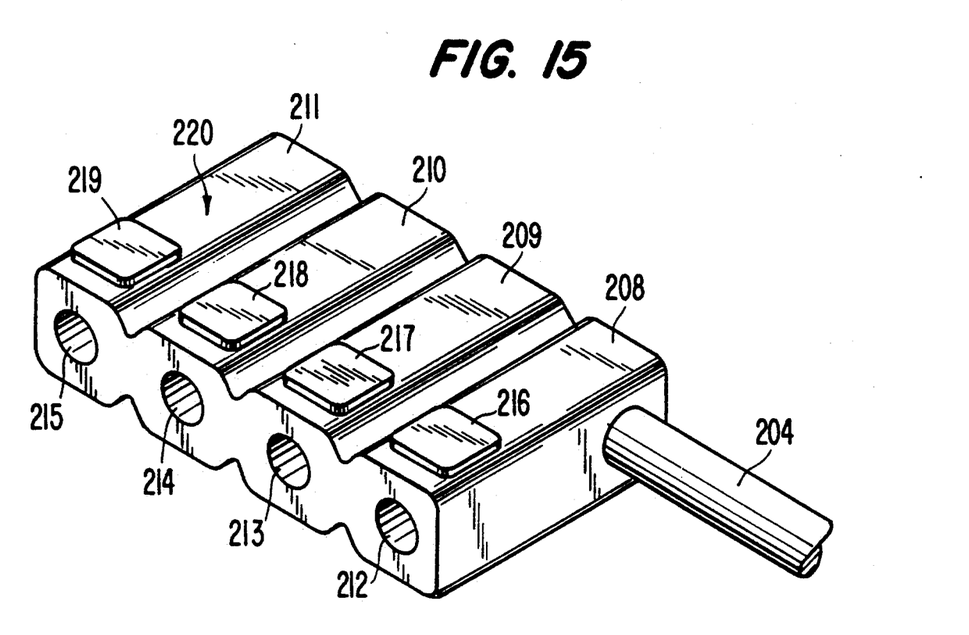
FIG. 15 is a perspective view of the connector assembly for use with the remote connector arrangement of FIGS. 14A and 14B.

As shown in FIGS. 14A and 14B, and in greater detail in FIG. 15, the plurality of connectors 206 may comprise a number of grouped connectors 208, 209, 210 and 211. While four such connectors have been illustrated, it is to be understood that such a remote lead assembly may be provided with more or fewer such connectors. The connectors 208-211 may be molded within a common housing, as denoted by reference character 220 in FIG. 15, which may be formed of a biocompatible material such as silicon rubber.

Each of connectors 208-211 may be formed of a connector 10, 10' or 10" as described previously with respect to FIGS. 2-13. In the arrangement illustrated in FIG. 15, each connector 208-211 has an aperture 212-215, respectively, into which a corresponding electrode lead tip (not shown) may be inserted. Where the connectors 208-211 are of the designs previously discussed with respect to FIGS. 2-10, a corresponding number of pads 216-219 are provided on housing 220 to permit manual operation of each connector 208-211, respectively, in the manner discussed above.

This aspect of the present invention contemplates use of other connectors, as well, in connection with the plurality of connectors 206 of remote lead assembly 202. For example, the set screw connector shown in FIG. 1 may be used for each of connectors 208-211. Accordingly, variations in the type and construction of the individual connectors are considered to be within the scope of the present invention with regard to the remote lead assembly arrangement illustrated in FIGS. 14-15.

While the above description contains many specificities, these are not limitations on the scope of the invention, but rather exemplifications of preferred embodiments thereof. For example, various types of materials may be used to form the connectors described herein, including titanium, stainless steel, tungsten or an alloy known as MP35N. Accordingly, the scope of the invention is to be construed in light of this description and the following claims.

What is claimed is:

1. An implantable conductive connector for coupling the proximal end of a pacemaker lead to a pacer housing, the connector comprising:
   first means for receiving the proximal end,
   second means resiliently engaging said first means for entrapping the proximal end between said first means and second means to provide electrical and mechanical coupling with the proximal end; and
   means for mechanically coupling together said first and said second means,
   said first and second means being resiliently disposed in a closed position prior to insertion of the proximal end into the connector, and being disposed in an open position, different from said closed position, upon insertion of the proximal end into the connector;
   said first means including a first hole and said second means including a second hole, said first and second holes being aligned with each other when the connector is in said open position and being offset from each other when the connector is in said closed position.

2. The connector recited in claim 1, wherein said first and said second means each comprises a generally flat portion terminated by a face portion,
   said first and second holes being disposed in said face portions of said first and second means, respectively, and
   said coupling means being disposed proximate the ends of said flat portions of said first and second means opposite to said face portions.

3. The connector as recited in claim 2, wherein said face portions of said first and second means include an interlocking tab means for controlling relative movement of said first and said second means.

4. The connector as recited in claim 3, further comprising a housing formed of an insulative biocompatible material that enclosed said first and said second means.

5. An electrode lead assembly for connecting an implantable pacemaker device to a proximal end of an electrode lead that is coupled to a remote electrode through a first length of wire, comprising:
   a lead comprising a second length of conductive flexible wire having first and second ends, said first end being adapted to be coupled to the pacemaker device; p1 means connected to said second end of said lead for coupling to the first length of wire; and
   a housing formed of an insulative biocompatible material that encloses said coupling means,
   said coupling means comprising:
   first means for receiving the proximal end; and second means for resiliently engaging said first means for entrapping the proximal end between said first means and said second means to provide electrical and mechanical coupling with the proximal end, said first and second means being resiliently disposed in a closed position prior to insertion of the electrode tip into the coupling means, and being disposed in an open position, different from said closed position, upon insertion of the electrode tip into the coupling means.

* * * * *